(12) United States Patent
Harp

(10) Patent No.: US 6,368,870 B1
(45) Date of Patent: Apr. 9, 2002

(54) CONTROLLED DIFFUSION ANALYSIS

(75) Inventor: Danial L. Harp, Berthoud, CO (US)

(73) Assignee: Hach Company, Loveland, CO (US)

( * ) Notice: Subject to any disclaimer, the term of this patent is extended or adjusted under 35 U.S.C. 154(b) by 0 days.

(21) Appl. No.: 09/326,406

(22) Filed: Jun. 4, 1999

(51) Int. Cl.$^7$ ................................................ G01N 1/18
(52) U.S. Cl. ................ 436/177; 436/109; 436/110; 436/111; 436/113; 436/114; 436/124; 436/62; 436/128; 436/130; 436/146; 436/147; 436/167; 436/168
(58) Field of Search ................ 436/62, 109, 110, 436/111, 113, 114, 124, 128, 130, 146, 147, 167, 168, 177; 422/58, 61

(56) References Cited

U.S. PATENT DOCUMENTS

| | | | | |
|---|---|---|---|---|
| 3,955,924 A | * | 5/1976 | Northmore et al. | 436/136 |
| 4,071,319 A | * | 1/1978 | Nugent | 436/128 |
| 4,409,182 A | * | 10/1983 | Macklem | 422/61 |
| 4,434,235 A | * | 2/1984 | Rabi et al. | 436/110 |
| 4,596,132 A | * | 6/1986 | Takami et al. | 73/23 |
| 5,320,807 A | * | 6/1994 | Brinton et al. | 422/61 |
| 5,447,688 A | * | 9/1995 | Moore | 422/56 |
| 5,563,352 A | * | 10/1996 | Helmig | 73/863.12 |
| 5,981,293 A | * | 11/1999 | Charlton | 436/177 |

* cited by examiner

Primary Examiner—Jill Warden
Assistant Examiner—LaToya I. Cross
(74) Attorney, Agent, or Firm—Dean P. Edmundson

(57) ABSTRACT

A method is described for determining the presence of a volatile component in a test sample. The method involves use of two separate vessels, one of which is capable of being placed wholly within the other vessel. The test sample is placed in the larger vessel, and an indicator solution is placed in the smaller, inner vessel. Then a gas-tight closure is placed on the top of the outer, larger vessel. The assembly is heated to an elevated temperature, whereby the volatile target analyte which is released from the test sample transfers to the inner vessel and is absorbed by the indicator solution. The indicator solution can be analyzed by means of a calorimeter, spectrophotometer, etc.

25 Claims, 6 Drawing Sheets

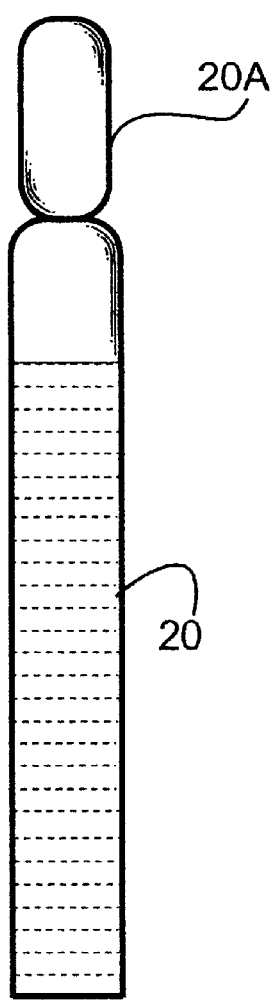
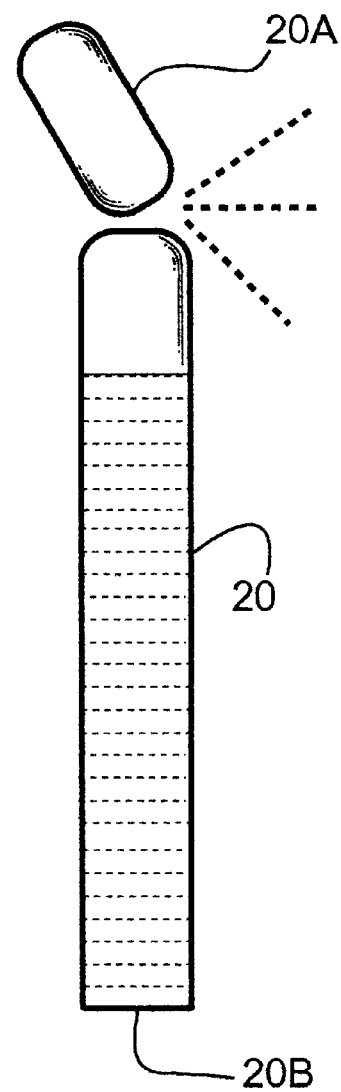
FIGURE 3          FIGURE 4

CONTROLLED DIFFUSION ANALYSIS

FIELD OF THE INVENTION

This invention relates to analysis of liquid samples (e.g. water) to determine the presence of a target analyte. More particularly, this invention relates to analysis of liquid samples to determine the amount of a volatile component produced or liberated from the liquid sample.

BACKGROUND OF THE INVENTION

It is often necessary or desirable to analyze a liquid sample (such as water) to determine the presence of various contaminants or components therein. For example, it is necessary to analyze water to determine the amount of carbonaceous material which may be present. This is often referred to as a "total carbon" test. In some applications, the total carbon test can be further differentiated to "organic carbon" and "inorganic carbon". Examples of organic carbon compounds would include carbon associated with amino acids or proteins. An example of inorganic carbon would be carbonates in water.

One conventional test method for determining the presence of carbon-containing material in water involves combustion of the sample to form carbon dioxide ($CO_2$) and determination of carbon dioxide by a nondispersive infrared analyzer. The disadvantages of such method include the high temperature, oxygen and catalysts needed to breakdown the carbon compounds to gaseous carbon dioxide and the necessity of purging, drying and carrier gas-transfer of the carbon dioxide to the analyzer. Instrumentation of this type is generally expensive and dedicated just for carbon measurements.

The principle of microdiffusion analysis is described by Conway, Edward J., *Microdiffusion Analysis and Volumetric Error*, Crosby Lockwood & Son Ltd., London, 5th Ed., 1962. It involves simple gaseous diffusion of a volatile substance from an outer chamber, where it exerts a certain tension, into an inner chamber, where the tension is zero on the surface of the absorbing fluid. At room temperature and at normal atmospheric pressure, the rate of diffusion of a volatile component is determined by its vapor pressure.

Conway determined that the diffusion process could rapidly reach completion using very small volumes of sample and reagents (typically less than 2 mL); thus, it was referred to as "microdiffusion". A major challenge to microdiffusion analysis was the precise volumetric measurements required for accurate results. Several micro-pipets and micro-buret designs were utilized by Conway for microdiffusion analysis.

Conway designed a special diffusion apparatus (a "unit") which in one form resembled a covered petri dish with concentric compartments. For example, in the microdiffusion procedure for ammonia, 1 mL of standard base solution is pipetted to the outer chamber of the unit. Then 1 mL of standard acid is pipetted to the inner chamber. A volume of sample (typically less than 1 mL) which contains ammonia, is added to the base reagent in the outer chamber. The unit lid is smeared with a fixative and then sealed, after which the unit is rotated in a circular motion to mix the sample with base solution. For ammonia, the unit is left to sit at room temperature or is continuously swirled in a rotating motion using an oscillating table. After a suitable time for absorption, the lid is removed and the contents of the inner chamber is removed for analysis, either by titration or calorimetric measurement.

Conway mainly employed isothermal diffusion, usually at room temperature. The rate of diffusion was controlled mainly by the volatile component's vapor pressure and small sample volume.

Conway's method for microdiffusion analyses does not allow much flexibility. Careful metering of reagents and sample volumes are required. Complete diffusion of the volatile component did not often occur using such method.

Kirk, P. L., *Anal. Chem.*, 22, 611 (1950) described a distillation-diffusion unit which utilized differential temperature for distillation. In the Kirk unit, the inner chamber, containing the absorbing media, is maintained at a lower temperature than the outer chamber, which contained the volatile component. The differential in temperature would aid the separation of constituents (such as volatile alcohols) for which there is no good chemical absorbent. However, in Kirk's design, it was necessary to prevent pressure developed during heating, which could blow the seal open. Thus, Kirk's unit incorporated an evacuation design to prevent pressure build-up in the test unit.

Other microdiffusion units are described by Koga et al., *Shika Gakuho*, 90(7), 979–82 (1990); Hinoide et al., *Journal of Dental Health*, 40, 254–55 (1990); Heyer, East German Patent DD 213065 (1984); and Grosse, Russian Patent SU 1623747 (1991). The Koga, et al. and the Hinoide, et al. units are of similar design to a Conway unit and are made of TEFLON® and include a screw-cap closure. Like the Conway unit, microdiffusion is optimized by a horizontal orientation to maximize the surface area of the exposed sample and by limiting the sample size. The TEFLON unit probably could not be used at temperatures above the reported 90° C., and it must be disassembled to allow access to the trapping solution in the inner chamber for the analysis.

The apparatus described by Heyer was designed for separation of volatile components of mixtures. The mixture is placed in a cylinder which can be heated. An absorption chamber, which contains a sealing liquid, surrounds the top of the cylinder. A bell jar is inverted over the absorption chamber which serves to trap and condense the volatile component into the sealing liquid. Heyer's apparatus is principally based on heat convection as an aid to separation of components. Isothermal diffusion would not work with this design. The seal is accomplished using a liquid trap which absorbs the volatile component. The heat and pressure employed with this design must be limited to quantitatively trap the volatile gas. The absorbed material must be transferred out of the absorption chamber for measurement.

Grosse describes a cylinder cup with a spout and concave bottom. The absorbing medium is placed into this cup. A smaller cup is placed on the concave support of the larger cup and contains the sample and releasing reagent(s). A dome cover is placed over the assembly which integrates airspace between the two cups. The stated advantage of his design is that the assembly can be heated to accelerate the diffusion process. Because of the seal design, however, there is a practical limitation on the amount of heat and pressure that can be used with such unit. For example, the weight of the dome lid and its contact with the larger cup floor would be factors for maintaining adequate sealing. Like Conway's unit, the Grosse unit is based on using a small sample volume and large surface areas to maximize the diffusion process. This necessitates the horizontal orientation of the device. It is also necessary to remove the trapped analyte from the absorption cup in order to analyze it.

The main objection to the use of micro-diffusion analyses has been the comparative slowness of the diffusion and the strict adherence to controlling factors which affect precision and accuracy of the method. Depending upon the particular unit used, isothermal diffusion could require up to 12 hours for complete transfer of the volatile component. Certain materials have a low vapor pressure and are difficult to diffuse isothermally.

There has not heretofore been provided a relatively simple and reliable controlled diffusion test method or procedure which has the features and advantages provided by the present invention.

SUMMARY OF THE INVENTION

In accordance with the present invention, there is provided an improved controlled diffusion test method for determining the presence and amount of a target analyte in a sample (which may be a liquid solution or a solid substance) which would volatize the sample analyte of interest. The test method involves the use of two separate tubular vessels of different diameters. The sample being tested is placed into the larger diameter tube or vessel, and an absorbing medium (which is a liquid solution) which serves as an indicator is placed in the smaller tube or vessel. Any necessary digestion reagents or reagents needed to volatize the analyte are added to the sample in the larger tube.

Then the smaller tube is placed inside of the larger tube, and a cap or closure member encloses the top end of the large tube and provides a gas-tight seal thereon. The assembly is then heated to an elevated temperature, whereby a volatile component (a target analyte) is produced or liberated from the test sample and enters into the open top of the smaller diameter tube where it is absorbed by the indicator.

Typically, the indicator changes color as it absorbs the target analyte. The extent of the color change may be easily measured optically to provide a quantitative determination of the amount of target analyte absorbed. For example, the extent of the color change can be measured with a spectrophotometer, a calorimeter, or a filter photometer.

The optical measurement can even be performed by passing a transverse light beam directly through both of the tubes without disassembly of the system when both the test sample and the indicator are liquids. This technique provides simplicity and avoids the need to separate the tubes or to remove any of the indicator from the inner tube, thereby avoiding possible spillage or contamination of the indicator.

The technique of the invention is useful for measuring a wide variety of target analytes, including for example, volatile amines, ammonia, antimony, arsenic, azide, cyanide, formaldehyde, halogens, ketones, tertiary nitrogen compounds, mercury, nitrates, nitrites, organic substances, phenols, sulfides, inorganic or organic halogen compounds, total nitrogen, oxygen demand, carbon, volatile organic carbon, total inorganic carbon, total organic carbon, particulate and non-purgable organic carbon, volatile acids, volatile alcohols, and other volatile organic compounds.

The techniques of the present invention provide a means for completely digesting hard-to-digest compounds, efficiently diffuse the resulting volatile component into a trapping media and measure the component concentration directly. The tube assemblies can be disposable, thereby avoiding the potential for contamination through re-use. The compactness of the system is also an advantage in laboratories where space is at a premium.

The invention does not require dedicated instrumentation such as is required with the conventional combustion-nondispersive infrared method. The invention uses spectrophotometers, calorimeters or filter photometers which are commonly available at analytical laboratories.

Since the instrumentation and skill level to perform the test of the invention is minimal, the cost per test is much less than the conventional test methods.

Other features and advantages of the method of the invention will be apparent from the following detailed description and the accompanying drawings.

BRIEF DESCRIPTION OF THE DRAWINGS

The invention is described in more detail hereinafter with reference to the accompanying drawings wherein like reference character refer to the same parts throughout the several views and in which:

FIG. 3 is a side elevational view of a preferred embodiment of an indicator tube which is useful in the invention;

FIG. 4 illustrates the opening of the tube of FIG. 3 by removing the top portion;

DETAILED DESCRIPTION OF THE INVENTION

Figure 1:
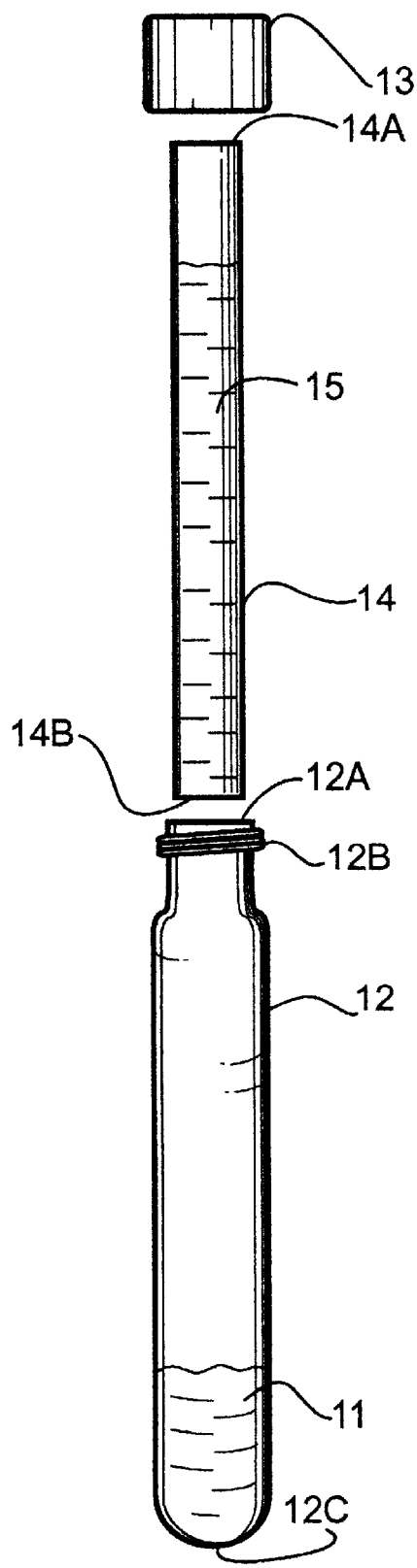
FIG. 1 is an exploded view illustrating one embodiment of apparatus which is useful in the techniques of this invention.
Figure 2:
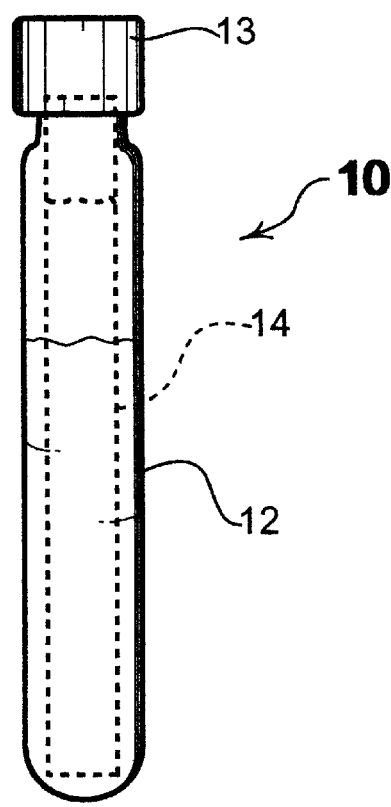
FIG. 2 is a side elevational view showing the assembled form of the components of FIG. 1.

In FIGS. 1 and 2 there is illustrated one embodiment of diffusion test assembly 10 which is useful in the invention. The assembly includes (a) a large tubular vessel 12 having an open top end 12A and a closed lower end 12C, (b) a smaller diameter tubular vessel 14 having an open top end 14A and a closed lower end 14B, and (c) a sealing cap or closure member 13 for enclosing and sealing the top end of vessel 12. Preferably the upper end of vessel 12 includes threads 12B so that the cap 13 can be threadably secured to the top of vessel 12. It is preferable that both the inner and outer vessels are light-transparent (or at least a portion of the walls are light-transparent so that a light beam can pass transversely therethrough).

A sample 11 to be tested (and any necessary reagents) are placed in the outer vessel 12, and an indicator 15 is placed in the inner vessel 14. Then the cap 13 is fitted onto the top of the vessel 12 to form a gas tight seal. The outer diameter and length of the inner tube are both smaller than the inner diameter and length of the outer tube such that the inner tube can be fitted wholly within the outer tube, and the cap member can be secured to the top of the outer tube to seal it.

There is sufficient space around the periphery of the inner tube that a volatile component liberated from the test sample in the outer tube can enter into the open end of the inner tube. When the test assembly is heated to an elevated temperature, the pressure inside of the assembly increases as the volatile component is produced or liberated. This increased pressure enhances the absorption of the volatile component in the indicator in the inner tube. No membrane is required to be included on the open end of the inner tube.

Figure 5:
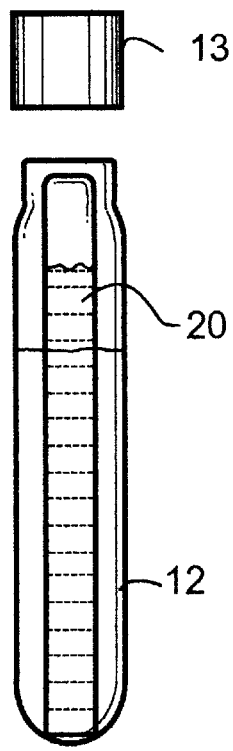
FIG. 5 shows the placement of the tube of FIG. 4 in a sample tube of larger diameter.

FIG. 3 illustrates an alternative embodiment of a tubular vessel 20 which can be used for the indicator. This type of vessel is filled with the appropriate liquid indicator and is sealed at the site of manufacture. The upper end 20A of the vessel is adapted to be broken off when one desires to access the indicator in the vessel. To facilitate the breaking off of the upper end, the periphery of the vessel is scored at the factory between the upper end 20A and the main body of the vessel. The upper end 20A is broken off as illustrated in FIG. 4. Then the vessel can be fitted inside of the larger vessel 12 as illustrated in FIG. 5.

Preferably the lower end 20B of vessel 20 is flat. This 20 feature assists in centering the lower end of vessel 20 inside of the larger vessel 12, and the upper end of vessel 20 is centered in the neck area of vessel 12, as illustrated in FIG. 5.

Figure 6:
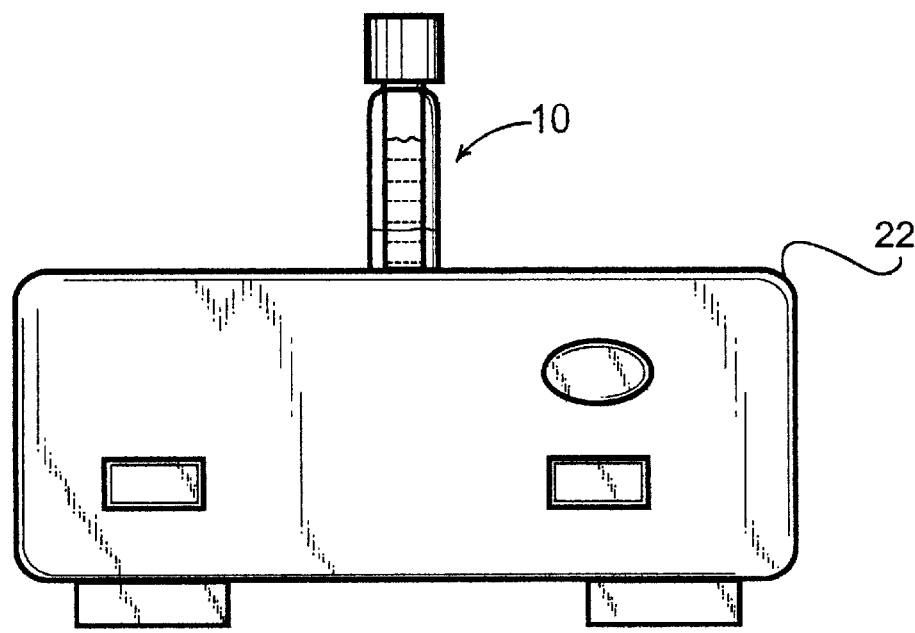
FIG. 6 shows the placement of the diffusion assembly of FIG. 5 in a heating block for heating the test sample to an elevated temperature for a given period of time.
Figure 7:
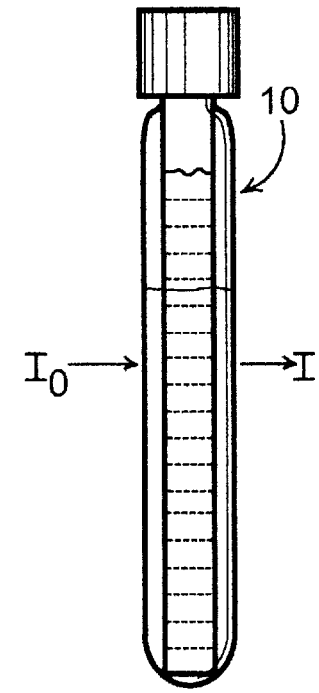
FIG. 7 illustrates the manner in which a light beam is passed transversely through the diffusion assembly of FIG. 5 after the target analyte has been produced or liberated from the test sample.

The test assembly is then heated to an elevated temperature in a heating block 22, for example, as illustrated in FIG. 6, for an appropriate period of time to enable the target analyte to be produced or liberated from the test sample in vessel 12 and absorbed in the indicator in vessel 20. Then the test assembly can be removed from the heat source and allowed to cool. Then a light beam can be passed transversely through the test assembly as illustrated in FIG. 7 to measure the amount of light absorbance by, or transmittance through, the target analyte in the indicator.

Figure 8:
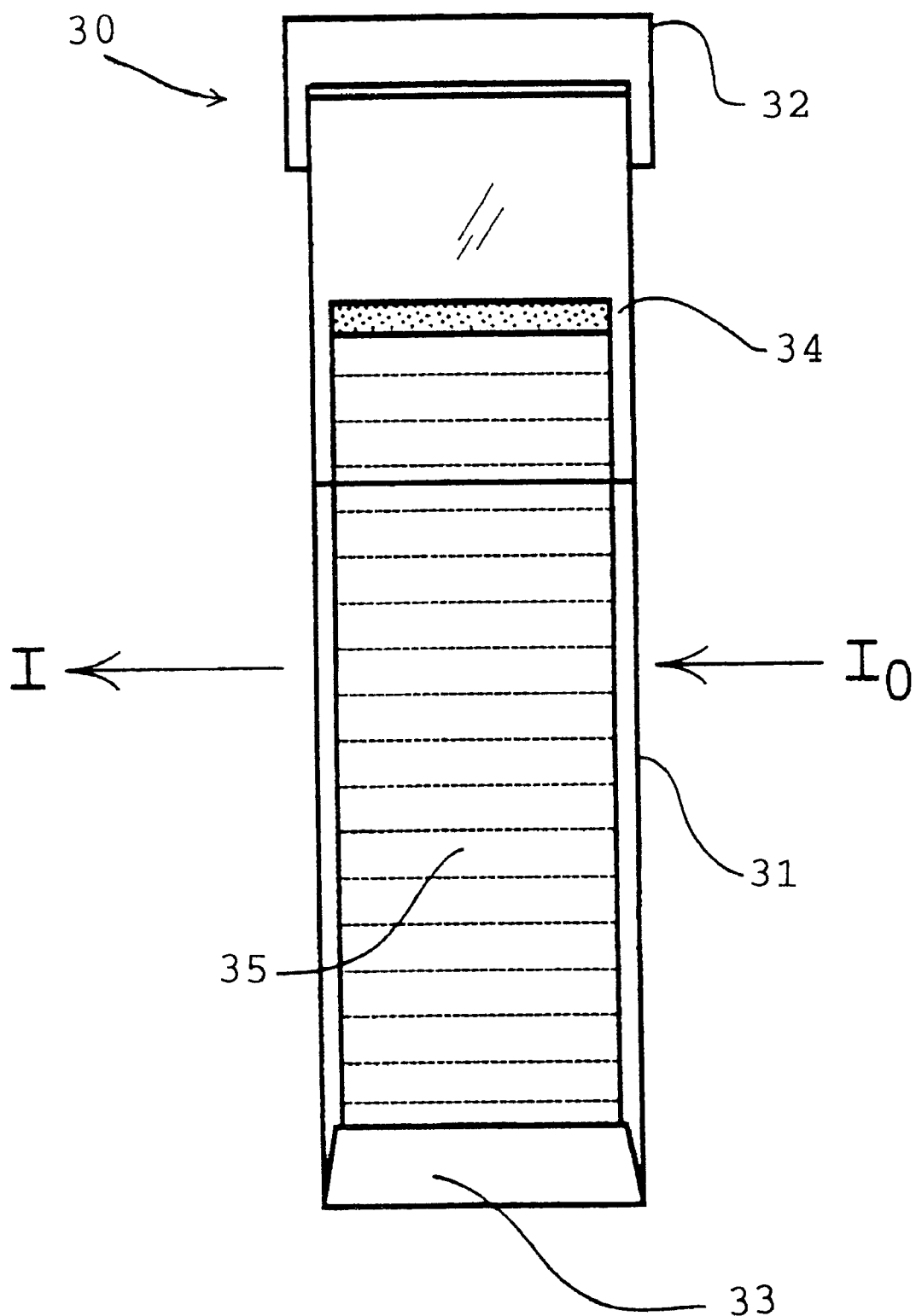
FIG. 8 illustrates another embodiment of a diffusion test assembly which is useful in this invention.

FIG. 8 illustrates another embodiment of a test assembly 30 which can be used in the present invention. The assembly includes an outer tubular vessel 31 and a smaller tubular vessel 35 which contains an indicator and is capable of fitting wholly within the outer vessel. A centering insert 33 may be included in the outer vessel to assist in centering the inner vessel with respect to the outer vessel. A porous hydrophobic membrane 34 may be fitted over the top end of the inner vessel, although this is not required. A cap or closure member 32 is secured on the top end of the outer vessel to form a gas-tight seal. The sample to be tested is placed in the outer tube, and the test assembly is heated to an elevated temperature for a period of time. After the assembly is cooled, it can be placed in an appropriate instrument where a light beam passes transversely through the entire assembly. There is no need to remove the inner vessel from the outer vessel, nor is it necessary to remove the indicator from the inner vessel for testing.

To illustrate the invention, calorimetric measurement of total carbon (TC) is discussed. The principle of the method is that the inorganic and organic carbon of a sample are digested in the presence of persulfate (either alkaline or acidic medium) to form carbon dioxide gas. The evolved carbon dioxide gas is then trapped in an aqueous solution which contains a pH indicator. The absorbed carbon dioxide forms carbonic acid. The pH indicator (before absorption of carbon dioxide) is in its de-protonated or basic form. As the absorbed carbon dioxide level increases, the hydrogen ion level will also increase, resulting in an increase of the protonated form of the indicator. The concentration of the total carbon originally in the sample is directly proportional to the color change of the indicator.

In practical application with the diffusion unit of the invention, the inner tube contains an aqueous pH indicator solution with a suitable pKa such as thymol blue (pKa=8.86 to 9.0), phenolphthalein (pKa=9.46 to 9.6), or p-xylenolphthalein (pKa=9.7). The pH indicator is slightly buffered to maintain the fully protonated form of the indicator, and a reducing agent (e.g. sodium thiosulfate) can be added to the indicator to prevent chlorine interference. A typical volume of the indicator in the inner vessel would be 3 milliliters (mL). The outer vessel would contain digestion reagents: a dilute acid (such as sulfuric, phosphoric, or hydrochloric acid) or alkaline (such as sodium, potassium or lithium hydroxide) reagent and persulfate (sodium, potassium or lithium salt). The volume of digestion solution is typically in the range of 1–5 mL.

In the operation of the unit for calorimetric total carbon determination, the inner vessel or tube and the outer vessel or tube are initially separate. A suitable amount of sample or blank is introduced into the digestion reagents in the outer tube. The tube containing the buffered pH indicator is inserted into the outer tube (which is threaded at its upper end) containing the digestion reagents and sample.

The dimensions and design of the inner tube are such that the inner tube is centered at the neck and at the conical bottom of the outer tube. This allows for vertical orientation of the inner tube parallel to the walls of the outer tube. The shorter length of the inner tube allows for a finite amount of headspace between the top of the inner tube and the cap on the outer tube for gaseous diffusion to occur.

The upper end of the outer tube is then sealed with a cap having an inert liner which is impervious to leakage up to about 300 psi. The assembled is placed in a temperature-controlled incubator or heated digestion block at an elevated temperature. The heated block digester is the preferred device due to the effective transfer of heat from the block to the contents of the outer tube. In the case of total carbon analysis, the temperature selected for digestion/diffusion is between 100 and 110° C. This selected temperature is a compromise, based on the time necessary to completely digest inorganic and organic carbon to carbon dioxide and the efficient transfer of carbon dioxide to the absorbing pH indicator. Although the rate of digestion and diffusion can be accelerated at higher temperatures and pressures, the stability of the pH indicator becomes a factor affecting the reproducability of the determination. Lower temperatures will require longer times for diffusion of carbon dioxide into the indicator.

During the heating process, a thermal gradient develops between the contents of the inner and outer vessels or tubes. The components of the outer vessel are at an elevated temperature relative to the temperature of the indicator in the inner vessel. The thermal differential between the two solutions promotes the efficient transfer of the volatile component (i.e. carbon dioxide) from the outer tube into the inner tube solution. Since the unit is completely sealed, the increased pressure generated during the heating period promotes the digestion and diffusion processes.

After a suitable period of heating (typically two hours) at 100–110° C., the digestion and diffusion processes in the sealed unit are complete. The unit is then allowed to cool to room temperature. Adequate cooling is required to minimize refractive index effects, when direct calorimetric measurements are made.

The light absorption of the indicator solution will change based on the concentration of carbon in the sample. The decrease in the original concentration of the deprotonated indicator, or the increase of the protonated form, or the sum or ratio of the two changes can be measured usually with an appropriate spectrophotometer, calorimeter, or filter photometer. It is not necessary to separate the inner tube from the outer tube for color measurement for most applications. Because the tube or vial assembly is self-centering, the unit can be placed directly into the instrument for light absorption measurements. Alternatively, the contents of the inner vial or tube can be removed (siphoned) and measured using a suitable spectrometer cell or measured by other methods of chemical analysis, including titration.

Colorimetric measurement is preferred but, if desired, one could instead measure for the presence of a target analyte with other means (such as an ion-selective probe, titration, turbidity, spectra analysis, potentiometric analysis, amperometric analysis, etc.).

EXAMPLE 1

In the determination of total carbon in a range of 0–700 mg/L carbon, 0.3 mL of zero-carbon water or a standard potassium acid phthalate solution is added to 4.0 mL of an acid digest reagent in the outer vessel. Potassium acid phthalate (KHP) is a standard source of carbon which is commonly used for total carbon or total organic carbon determinations. A blank (zero-carbon water) is required for single wavelength measurements.

Next, a small quantity of solid potassium persulfate (0.1 g) is added to the digestion solution. A known addition of a freshly prepared persulfate reagent solution could also be used. The digestion solution contents are swirled to mix.

The inner tube is an ampoule containing 3.0 mL of a slightly buffered thymol blue reagent solution. The ampoule top is snapped off and the ampoule is inserted into the outer vessel which contains the digestion solution. The open top of the inner ampoule is at a level higher than the upper surface of the digestion solution in the outer vessel.

The complete assembly is sealed with an appropriate cap which forms a gas-tight seal on the top of the outer vessel. The assembly is placed in a temperature-controlled heater block set to 103–105° C. After heating for a two hour period, the tube assembly is removed and allowed to cool to room temperature.

After cooling, the tube assembly containing the blank is placed into a suitable spectrophotometer set at a wavelength setting of 598 nm. The light absorption of the blank is measured versus a colorless reference (DI water) or set to read "zero" absorbance.

The tube assembly containing the KHP standard is then placed into the spectrophotometer and its light absorption is measured against the colorless reference or versus the blank.

Figure 9:
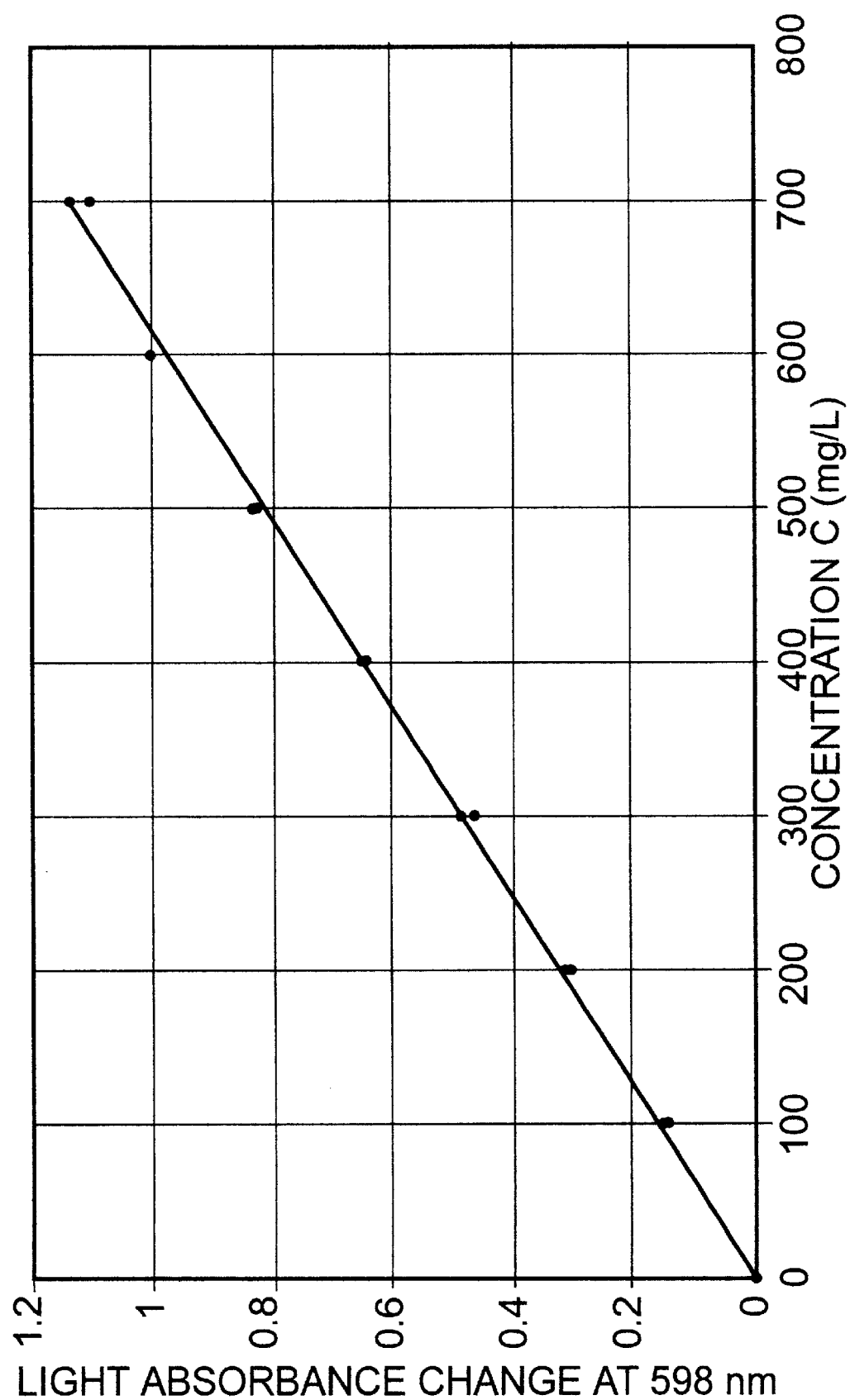
FIG. 9 is a graph illustrating determination of total carbon present in a series of standard water samples having a range of carbon concentration from 0 to 700 mg/L, plotted as absorbance change (at one wavelength)

The difference between the blank and standard KHP absorbances at 598 nm (i.e., dA598) is proportional to the carbon concentration as indicated in FIG. 9. The calibration graph can be used to determine the mg/L total carbon in a test sample which is treated in accordance with the procedure discussed above in this example.

EXAMPLE 2

In the determination of total organic carbon in a range of 0–20 mg/L carbon, 3.0 mL of a standard potassium acid phthalate solution is added to 1.0 mL of an acid digest reagent in the outer vessel. The acid digest reagent is of higher acidity than that used in Example 1.

Next, a small quantity of solid potassium persulfate (0.1 g) is added to the digestion solution. A known addition of a freshly prepared persulfate reagent solution could also be used. The digestion solution contents are swirled to mix.

The inner tube ampoule contains 3.0 mL of a slightly buffered thymol blue reagent solution. The ampoule top is snapped off and the ampoule is inserted into the outer vessel which contains the digestion solution.

The complete assembly is sealed with an appropriate cap member placed on the top of the outer vessel to form a gas-tight seal. The assembly is placed into a temperature-controlled heater block set to 103–105° C. After heating for two hours, the tube assembly is removed and allowed to cool to room temperature.

After cooling, the tube assembly containing the blank is placed into a suitable spectrophotometer capable of multi-wavelength measurements at 598 nm and 430 nm. The light absorption at each wavelength is zeroed using colorless DI water.

The tube assembly containing the KHP standard is then placed into the spectrophotometer and its light absorption is measured at 598 nm and 430 nm against the colorless reference.

Figure 10:
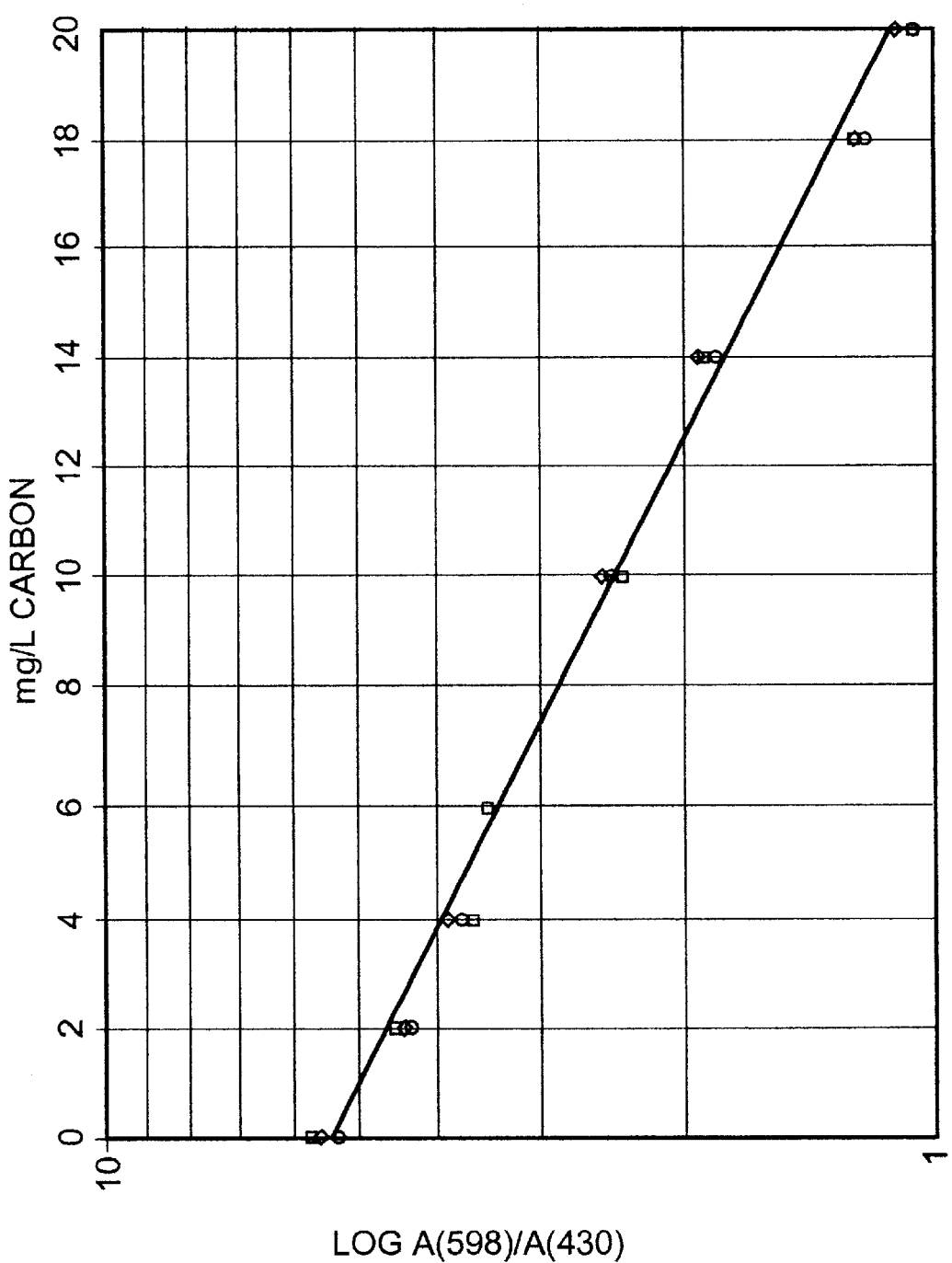
FIG. 10 is a graph illustrating determination of total carbon present in a series of standard water samples having a range of carbon concentration from 0 to 20 mg/L, plotted as a ratio of absorbance at two separate wavelengths.

As shown in FIG. 10, the ratio of the two absorption peaks (A-598/A-430) is exponentially proportioned to the mg/L KHP carbon. The peak ratio method compensates for any variations due to thermal degradation of the indicator, path length differences between different tube assemblies, or light scattering. The peak ratio method of measurement does not require a blank determination to be performed.

The sample TOC concentration can be determined by pre-acidifying a small portion of sample to pH less than 4 and then mixing vigorously to sparge the sample of the resulting $CO_2$. Sample pre-acidification converts the inorganic carbon to carbon dioxide. What remains in the sample is non-volatile organic carbon. The sample can be treated as above and the calibration graph is then used to estimate the sample TOC concentration.

Other variants are possible without departing from the scope of this invention. For example, it has been observed that the relative diameter of the inner tube or vessel as compared to the inner diameter of the outer tube or vessel is not critical in the practice of this invention.

What is claimed is:

1. A method for determining the presence of a volatile component in a test sample, the method comprising the steps of:

(a) providing a first vessel with an open top and a gas-tight closure member for said top;

(b) providing a second vessel with an open top and a closed lower end, wherein the length and diameter of said second vessel are less than the corresponding length and diameter of said first vessel such that said second vessel can be fitted wholly within said first vessel; wherein said second vessel includes liquid indicator means capable of indicating the presence of said volatile component;

(c) introducing said test sample into said first vessel along with reagent means capable of liberating said volatile component;

(d) introducing said second vessel into said first vessel;

(e) installing said closure member on said top of said first vessel;

(f) heating said sample in said first vessel to an elevated temperature, whereby said volatile component in said first vessel passes into said second vessel to cause a change in said indicator; and (g) measuring said change in said indicator to determine the amount of said volatile component produced from said sample wherein said elevated temperature is sufficient to liberate volatile components from the first vessel.

2. The method in accordance with claim 1, wherein said indicator is capable of absorbing said volatile component.

3. The method in accordance with claim 1, wherein said sample contains organic material, and wherein said reagent means is capable of digesting said organic material to produce carbon dioxide.

4. The method in accordance with claim 3, wherein said elevated temperature is in the range of about 100 to 150° C.

5. The method in accordance with claim 1, wherein said top of said first vessel is threaded, and wherein said closure member is threadably fitted on said top.

6. The method in accordance with claim 1, wherein the space between said open top of said second vessel and said open top of said first vessel is in the range of about 2 to 10 mm.

7. The method in accordance with claim 1, wherein said first and second vessels are coaxially aligned.

8. The method in accordance with claim 7, wherein said first vessel has a rounded lower end.

9. The method in accordance with claim 1, wherein said change in said indicator comprises a color change.

10. The method in accordance with claim 9, wherein said color change is measured with a spectrophotometer, a calorimeter, or a filter photometer.

11. The method in accordance with claim 10, wherein said first and second vessels are light-transparent, and wherein color change is measured by means of a light beam passing transversely through said first and second vessels.

12. The method in accordance with claim 1, wherein said second vessel has a flat lower end.

13. The method in accordance with claim 1, wherein said first and second vessels include walls which are parallel to each other.

14. The method in accordance with claim 1, wherein said volatile component comprises ammonia.

15. The method in accordance with claim 1, wherein said volatile component comprises cyanide.

16. The method in accordance with claim 1, wherein said volatile component comprises fluoride.

17. A method for determining the presence of a volatile target analyte in a liquid sample, the method comprising the steps of:

(a) providing a first vessel with an open top end and a gastight closure member for said top;

(b) providing a second vessel with an open top and a closed lower end, wherein the length and diameter of said second vessel are less than the corresponding length and diameter of said first vessel such that said second vessel can be fitted wholly within said first vessel; wherein said second vessel includes liquid indicator means capable of indicating the presence of said target analyte;

(c) introducing said liquid sample into said first vessel along with reagent means capable of liberating said target analyte;

(d) introducing said second vessel into said first vessel;

(e) installing said closure member on said top of said first vessel;

(f) heating said sample in said first vessel to an elevated temperature, whereby said target analyte liberated from said first vessel passes into said second vessel to cause a change in said indicator means; and (g) measuring said change in said indicator means to determine the amount of said target analyte produced from said sample wherein said elevated temperature is sufficient to liberate volatile components from the first vessel.

18. The method in accordance with claim 17, wherein said liquid sample comprises water.

19. The method in accordance with claim 18, wherein said target analyte comprises carbon.

20. The method in accordance with claim 19, wherein said carbon is produced from said sample in the form of carbon dioxide.

21. The method in accordance with claim 17, wherein said first and second vessels include walls which are parallel to each other.

22. The method in accordance with claim 17, wherein said change in said indicator means comprises a color change, and wherein said color change is measured by means of a light beam passing transversely through said first and second vessels.

23. The method in accordance with claim 20, wherein said reagent means comprises a persulfate compound.

24. The method in accordance with claim 23, wherein said indicator means comprises an aqueous solution of a pH sensitive compound.

25. The method in accordance with claim 24, wherein said indicator means comprises phenolphthalein.

* * * * *